United States Patent [19]

Shibata

[11] Patent Number: 5,417,648
[45] Date of Patent: May 23, 1995

[54] METHOD AND APPARATUS FOR GENERATING PULSATING BLOOD FLOW IN A DIALYZER CIRCUIT

[75] Inventor: Takeru Shibata, Yokohama, Japan

[73] Assignee: Saitteku Kabushiki Kaisha, Kamakura, Japan

[21] Appl. No.: 902,581

[22] Filed: Jun. 22, 1992

[51] Int. Cl.⁶ .................................... A61B 1/00
[52] U.S. Cl. .............................. 604/4; 604/34
[58] Field of Search .............. 604/4, 5, 6, 30, 33, 604/34; 417/474, 477, 412, 413 R

[56] References Cited

U.S. PATENT DOCUMENTS

| | | | |
|---|---|---|---|
| 3,511,238 | 5/1970 | Wrangell | 604/4 |
| 3,579,441 | 5/1971 | Brown | 604/4 X |
| 3,985,134 | 10/1976 | Lissot et al. | 604/34 X |
| 4,524,802 | 6/1985 | Lawrence et al. | 604/34 X |
| 4,852,551 | 8/1989 | Opie et al. | 604/34 X |
| 4,963,131 | 10/1990 | Wortrich | 604/34 |

*Primary Examiner*—Sam Rimell
*Attorney, Agent, or Firm*—Wenderoth, Lind & Ponack

[57] ABSTRACT

An apparatus for generating a pulsation flow into a blood dialyzer in a blood dialyzing apparatus, has a pulsation flow generating apparatus for intermittently pressurizing and releasing a blood circuit. It also has a speed controller for controlling an operation speed of the pulsation flow generating apparatus. A method for charging blood into a blood dialyzer is also disclosed.

10 Claims, 3 Drawing Sheets

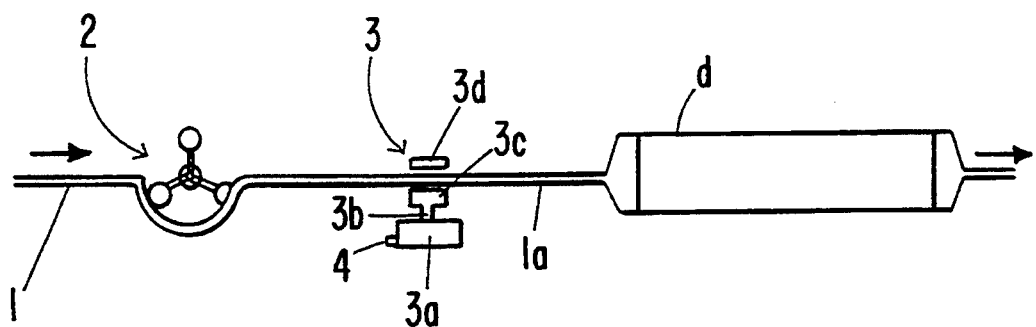
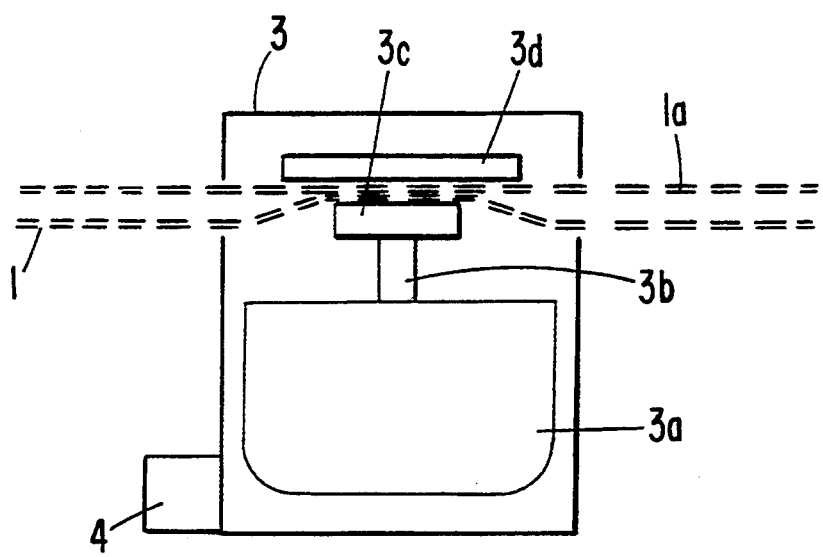

METHOD AND APPARATUS FOR GENERATING PULSATING BLOOD FLOW IN A DIALYZER CIRCUIT

BACKGROUND OF THE INVENTION

This invention relates to a medical treatment, and particularly to a blood dialysis. Furthermore, it relates to an apparatus for charging blood into a blood dialyzer, and a method for charging blood therein.

In general, blood is most easily coagulated at a blood inlet portion and a blood outlet portion (header) of a hollow yarn type blood dialyzer. Therefore, various proposals have heretofore been made in order to solve this problem, as discussed, for example, in Japanese Patent No. 1267833, Japanese Patent Publication No. Sho 62-54510, and Japanese Laid-Open (Kokai) Utility Model Application No. Sho 63-100051. In these publications, it is proposed to improve the configuration of a header portion in order to prevent blood from being coagulated at the header portion.

In an actual blood dialyzing operation, a flow rate of blood flowing in the blood dialyzer can range widely from 100 to 300 ml per minute, and in addition, consistency of blood differs for each individual patient.

On the other hand, this consistency of blood varies with the passage of time during the dialyzing operation. Therefore, a simple modification made to the configuration of the header portion is not enough to cope with all requirements under different conditions.

It is known that blood is readily coagulated when it contacts foreign matter outside the body. Particularly, when the flow of blood is slowed down or stagnated, the blood begins to coagulate at that spot.

In the case where blood is circulated outside of the body during a blood dialyzing operation, blood is most easily coagulated at a header portion h of a blood dialyzer shown in FIG. 2, because the blood coming from a blood circuit 1 is charged into the wide header portion h having an inner diameter of 40 to 50mm through a narrow inlet port i having an inner diameter of 3 to 4mm, and the blood flow is suddenly slowed down.

Specifically, the blood flowing through a central portion of the header h flows fast linearly from the inlet port. However, since the blood flow is stagnated at an area near the circumference of the header h, the blood begins to coagulate in a ring pattern first from the area near the circumference of the header, and then the blood coagulation is gradually spread towards the center of the header h.

When the blood coagulation is further spread to block an inlet of a dialyzing film of the hollow yarn, the blood in the hollow yarn is stopped from flowing and therefore becomes coagulated. In order to circulate the blood safely outside of the body without coagulation, a blood anti-coagulation agent is used. However, this chemical agent is sometimes accompanied by a side reaction. Particularly, if this is used for a patient suffering from a hemorrhagic concurrent disease or a patient before or after an operation, there is a risk of bleeding, and therefore the amount of use of the anti-coagulation agent must be reduced as much as possible.

SUMMARY OF THE INVENTION

It is therefore an object of the present invention to provide, in order to obviate the above-mentioned problems inherent in the prior art, an apparatus for generating blood pulsation flow into a dialyzer and a method for charging blood pulsation flow into a dialyzer, in which blood coagulation normally generated at the circumferential portion of a header is restrained by intermittently increasing a charging speed of the blood into the blood dialyzer.

To achieve the above object, according to one aspect of the present invention, there is essentially provided an apparatus for generating a pulsation flow into a blood dialyzer in a blood dialyzing apparatus, comprising a pulsating flow generating apparatus for intermittently pressurizing and releasing a blood circuit, and speed control means for controlling an operation speed of the pulsating flow generating apparatus.

According to another aspect of the present invention, there is also provided a method for charging a pulsating flow of blood into a blood dialyzer comprising intermittently pressurizing and releasing a blood circuit by using a pulsating flow generating apparatus in a blood dialyzing apparatus, and electrically controlling an operation speed of the pulsating flow generating apparatus.

Since an apparatus for generating a pulsating flow of blood into a blood dialyzer and a method for charging blood therein according to the present invention is embodied as mentioned above, the problem of blood coagulation during a blood dialyzing operation is considerably improved.

A mechanism for generating the blood coagulation is as follows. If the blood flowing pattern is hardly changed, fiblin and blood platelets as components for coagulating blood begin to deposit onto the surface of foreign matter at a spot where the blood flow is stagnated, and the blood coagulation spreads around the deposit which acts as a core.

In the system of the present invention, the blood flowing pattern is changed by intermittently varying the flowing speed of the blood, and a kind of washing effect is exhibited to the surface of the foreign matter by an instantaneous high speed flowing of blood in order to prevent the blood from being coagulated.

BRIEF DESCRIPTION OF THE DRAWINGS

FIG. 1 is a schematic view showing a blood dialyzing apparatus incorporated with a blood pulsating flow generating apparatus of the present invention;

FIG. 3 is a partly sectional side view of one embodiment of the pulsating flow generating apparatus according to the present invention, showing a crushed state of a tube of a blood circuit crushed by the pulsating flow generating apparatus.

DETAILED DESCRIPTION OF THE EMBODIMENT

One embodiment of an apparatus for generating a blood pulsation flow and a method for charging blood into a blood dialyzer according to the present invention will now be described in detail.

Figure 2:
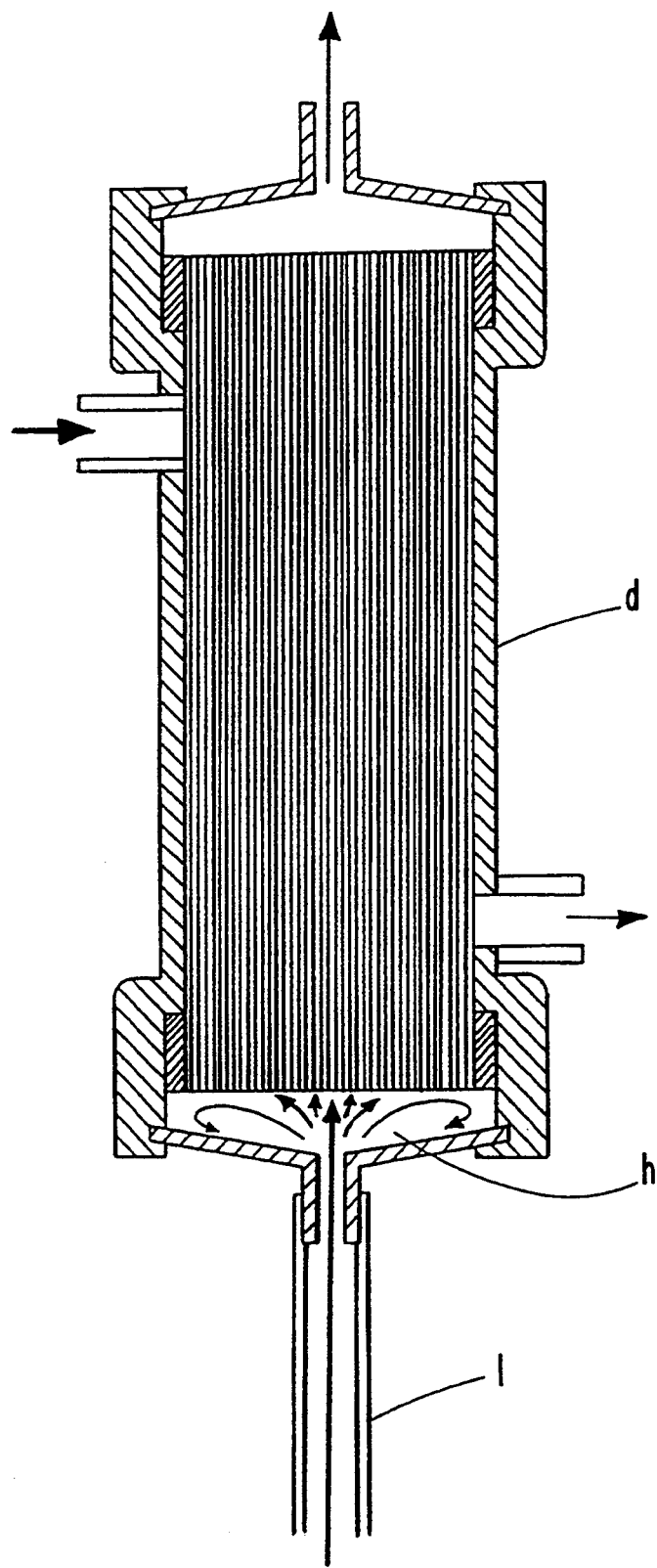
FIG. 2 is a side sectional view of a blood dialyzer.

FIG. 1 shows a schematic view of a blood dialyzing apparatus incorporated with a pulsation flow blood charging apparatus according to the present invention, and FIG. 2 shows a side sectional view of the blood dialyzer.

Figure 4:
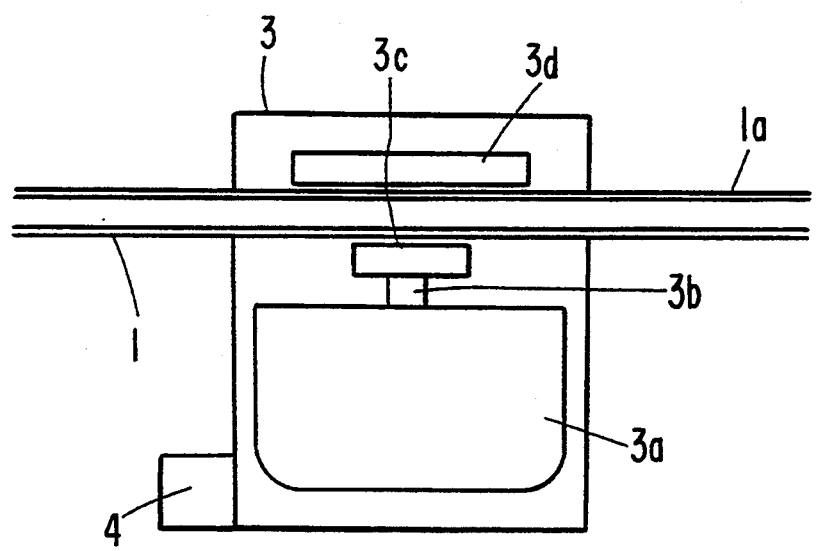
FIG. 4 is a partly sectional side view of the embodiment of the pulsating flow generating apparatus shown in FIG. 3, but showing a released state of the tube of the blood circuit released by the pulsating flow generating apparatus.

FIG. 3 is a partly sectional side view of one embodiment of the pulsation flow generating apparatus according to the present invention, showing a crushed state of a blood circuit crushed by the pulsation flow generating apparatus, and FIG. 4 is a partly sectional side view of the embodiment of the pulsation flow generating apparatus shown in FIG. 3, but showing a released state of the tube of the blood circuit released by the pulsation flow generating apparatus.

This embodiment functions to instantaneously pressurize a plastic tube of a blood circuit 1 and then immediately release the same. As for a construction for pressurizing the blood tube, various methods can be contemplated. In this embodiment, an electromagnetic driving device 3a is used as a power source for activating a piston 3b upwardly and downwardly.

The pulsation flow generating apparatus 3 thus constructed is disposed at a blood circuit 1a between a blood pump 2 and a blood dialyzer as shown in FIG. 1. In the foregoing arrangement, the blood circuit 1a is instantaneously sandwiched (pinched) between a stationary pinching member 3c and a movable pinching member mounted on the piston 3b, 3d and is then instantaneously released, repeatedly. As a result, a pulsation flow is generated, and blood is charged into the blood dialyzer.

The frequency or number of pulsations per minute can be properly set by a speed adjustment means 4 which constitutes a part of the present apparatus.

As apparent from the foregoing description, according to the present invention, an apparatus for generating a pulsation flow into a blood dialyzer in a blood dialyzing apparatus, comprises a pulsation flow generating apparatus for intermittently pressurizing and releasing a blood circuit, and speed control means for controlling an operation speed of the pulsation flow generating apparatus. Also, according to the present invention, a method for charging a pulsating flow of blood into a blood dialyzer comprises intermittently pressurizing and releasing a blood circuit by use of a pulsation flow generating apparatus in a blood dialyzing apparatus, and electrically controlling an operation speed of the pulsation flow generating apparatus.

Accordingly, a blood flow having a sufficient amount of pulsation is charged into the header. As a result, the stagnation of blood near the circumference of the header can be intermittently removed, and the blood can be more uniformly flowed in the hollow yarn at a spot near the circumference.

That is, the blood is charged into the blood dialyzer by a blood pump through a blood circuit. Although the flow of the blood is normally slightly pulsating due to operation of the blood pump, this slight pulsation is not strong enough to restrain the coagulation of blood.

Therefore, in order to maintain a stronger pulsation in the blood flow, the pulsation flow generating apparatus is disposed between the blood pump and the blood dialyzer. The pulsation flow generating apparatus is adapted to instantaneously pressurize the blood circuit in order to vary the flow rate and speed of the blood.

The blood pressurized and fed by the pulsation flow generating apparatus is added to the blood supplied by the blood pump. As a result, a fast flow takes place instantaneously to generate a pulsating flow, and this pulsating flow is charged into the blood dialyzer. By intermittently continuously effecting this operation, the blood flow is effectively made a pulsating flow.

Furthermore, this pulsating flow functions to prevent the deposition of the blood components onto the surface of the dialyzing film. This is quite effective when the blood dialyzer is re-used. On the other hand, this pulsation flow is also effective for washing the blood circuit and blood dialyzer and removing air (filling by means of a physiological saline (salt) solution) beforehand, and for returning the blood after the dialyzing operation. Indeed, this pulsating flow is indispensable for automatic filing and automatic returning of blood.

The present invention is not limited to the above embodiment, and various modifications can be made.

What is claimed is:

1. An apparatus for treating blood, comprising:
   a blood dialyzer having an inlet port and an outlet port;
   an inlet blood circuit connected to said inlet port of said blood dialyzer for feeding blood into said inlet port of said blood dialyzer;
   a blood pump operably coupled with said inlet blood circuit upstream of said inlet port of said blood dialyzer; and
   a pulsating flow generating apparatus, operably coupled to and interposed in said inlet blood circuit at a location between said inlet port of said blood dialyzer and said blood pump, for causing a flow of blood from said blood pump to said inlet port of said blood dialyzer to be pulsated by intermittently pressurizing and releasing said inlet blood circuit.

2. An apparatus as recited in claim 1, further comprising a speed control means for adjusting a number of pulsations per minute caused in the flow of blood from said blood pump into said inlet port of said blood dialyzer.

3. An apparatus as recited in claim 1, wherein
   said pulsating flow generating apparatus comprises a stationary pinching member positioned on a first side of said inlet blood circuit, a movable pinching member positioned on a second side of said inlet blood circuit opposite said stationary pinching member, and a driving means for intermittently moving said movable pinching member toward and away from said stationary pinching member.

4. An apparatus as recited in claim 3, wherein
   said driving means comprises a piston fixed to said movable pinching member, and an electromagnetic driving device operable coupled to said piston.

5. An apparatus for treating blood, comprising:
   a blood dialyzer having an inlet port and an outlet port;
   an inlet blood circuit connected to said inlet port of said blood dialyzer for feeding blood into said inlet port of said blood dialyzer;
   a blood pump operably coupled with said inlet blood circuit upstream of said inlet port of said blood dialyzer; and
   pulsation means for causing a flow of blood from said blood pump into said inlet port of said dialyzer to be pulsated by intermittently pressurizing and releasing said inlet blood circuit at a location of said inlet blood circuit between said inlet port of said blood dialyzer and said blood pump.

6. An apparatus as recited in claim 5, further comprising
   a speed control means for adjusting a number of pulsations per minute caused in the flow of blood from said blood pump into said inlet port of said blood dialyzer.

7. An apparatus as recited in claim 5, wherein said pulsation means comprises a stationary pinching member positioned on a first side of said inlet blood circuit, a movable pinching member positioned on a second side of said inlet blood circuit opposite said stationary pinching member, and a driving means for intermittently moving said movable pinching member toward and away from said stationary pinching member.

8. An apparatus as recited in claim 7, wherein said driving means comprises a piston fixed to said movable pinching member, and an electromagnetic driving device operable coupled to said piston.

9. A method for treating blood, comprising:
providing a blood dialyzer having an inlet port and an outlet port;
providing an inlet blood circuit connected to said inlet port of said blood dialyzer for feeding blood into said inlet port of said blood dialyzer;
operably coupling a blood pump to said inlet blood circuit upstream of said inlet port of said blood dialyzer, and operating said blood pump to charge the blood into said inlet port of said blood dialyzer; and
intermittently pressurizing and releasing said inlet blood circuit at a location between said inlet port of said blood dialyzer and said blood pump to cause the blood flowing from said blood pump into said inlet port of said blood dialyzer to be pulsated.

10. A method as recited in claim 9, further comprising electrically controlling a number of pulsations per minute caused in the flow of blood from said blood pump to said inlet port of said blood dialyzer.

* * * * *